(12) United States Patent
Alvarez Martin et al.

(10) Patent No.: US 10,975,414 B2
(45) Date of Patent: Apr. 13, 2021

(54) DECONTAMINATION SURROGATE MICROORGANISMS

(71) Applicant: NOVOLYZE, Daix (FR)

(72) Inventors: Pablo Alvarez Martin, Arc sur Tille (FR); Karim-Franck Khinouche, Dijon (FR)

(73) Assignee: NOVOLYZE, Daix (FR)

( * ) Notice: Subject to any disclaimer, the term of this patent is extended or adjusted under 35 U.S.C. 154(b) by 139 days.

(21) Appl. No.: 16/091,733

(22) PCT Filed: Apr. 28, 2017

(86) PCT No.: PCT/EP2017/060186
§ 371 (c)(1),
(2) Date: Oct. 5, 2018

(87) PCT Pub. No.: WO2017/186907
PCT Pub. Date: Nov. 2, 2017

(65) Prior Publication Data
US 2019/0153504 A1 May 23, 2019

(30) Foreign Application Priority Data

Apr. 29, 2016 (FR) .................................... 1653914

(51) Int. Cl.
| | | |
|---|---|---|
| *C12Q 1/22* | (2006.01) | |
| *C12N 1/20* | (2006.01) | |
| *A23C 3/03* | (2006.01) | |
| *A23L 3/16* | (2006.01) | |
| *A23B 9/02* | (2006.01) | |
| *C12R 1/01* | (2006.01) | |
| *C12M 1/12* | (2006.01) | |
| *C12Q 1/04* | (2006.01) | |
| *C12R 1/18* | (2006.01) | |

(52) U.S. Cl.
CPC .................. *C12Q 1/22* (2013.01); *A23B 9/02* (2013.01); *A23C 3/03* (2013.01); *A23L 3/165* (2013.01); *C12M 37/06* (2013.01); *C12N 1/20* (2013.01); *C12Q 1/04* (2013.01); *C12R 1/01* (2013.01); *C12R 1/18* (2013.01); *A23V 2002/00* (2013.01)

(58) Field of Classification Search
None
See application file for complete search history.

(56) References Cited

FOREIGN PATENT DOCUMENTS

WO   WO02090904 A2   11/2002

OTHER PUBLICATIONS

Jay, James M; et al; "Indicators of food microbial quality and safety" Modern Food Microbiology, 473-495, 2005 (Year: 2005).*
Rodriguez et al. "Surrogates for validation of electron beam irradiation of foods", International Journal of Food Microbiology, 2006, vol. 110, pp. 117-122.

(Continued)

*Primary Examiner* — David W Berke-Schlessel
(74) *Attorney, Agent, or Firm* — BCF, LLP

(57) ABSTRACT

The invention relates to the validation of decontamination processes and in particular to new surrogate organisms and mixtures of said microorganisms used for validating the decontamination processes.

14 Claims, 5 Drawing Sheets

(56) References Cited

OTHER PUBLICATIONS

Fudge et al. "The Isolation and Identification of Pantoea dispersa strain JFS as a Non-Pathogenic Surrogate for *Salmonella typhimurium* Phage Type 42 in Flour", Internationa Journal of Food Microbiology, 2016, vol. 219, pp. 1-6.

Borowski et al. "Validation of Ground-and-Formed Beef Jerky Processes Using Commercial Lactic Acid Bacteria Starter Cultures as Pathogen Surrogates", Journal of Food Protection, 2009, vol. 72, No. 6, pp. 1234-1247.

Enache et al. "Development of a Dry Inoculation Method for Thermal Challenge Studies in Low-Moisture Foods by Using Talc as a Carrier for *Salmonella* and a Surrogate (*Enterococcus faecium*)", Journal of Food Protection, 2015, vol. 78, No. 6, pp. 1106-1112.

Ceylan et al. "Evaluating Pediococcus acidilactici and Enterococcus faecium NRRL B-2354 as Thermal Surrogate Microorganisms for *Salmonella* for In-Plant Validation Studies of Low-Moisture Pet Food Products", Journal of Food Protection, 2015, vol. 78, No. 5, pp. 934-939.

Garcia-Hernandez et al., "Development and validation of a surrogate strain cocktail to evaluate bactericidal effects of pressure on verotoxigenic *Escherichia coli*", International Journal of Food Microbiology, 2015, vol. 205, pp. 16-22.

Guidelines for Using Enterococcus faecium NRRL B-2354 as a Surrogate Microorganism in Almond Process Validation, California Almonds, Almond Board of California Guideline, Jul. 2014.

Gurtler et al. "Selection of surrogate bacteria in place of *E. coli* O157:H7 and *Salmonella typhimurium* for pulsed electric field treatment of orange juice", International Journal of Food Microbiology, 2010, vol. 139, pp. 1-8.

Kopit et al. "Safety of the Surrogate Microorganism Enterococcus faecium NRRL B-2354 for Use in Thermal Process Validation", Applied Environmental Microbiology, Mar. 2014, vol. 80, No. 6, pp. 1899-1909.

Niebuhr et al. Evaluation of Nonpathogenic Surrogate Bacteria as Process Validation Indicators for *Salmonella* enteric for Selected Antimicrobial Treatments, Cold Storage and Fermentation in Meat, Journal of Food Protection, 2008, vol. 71, No. 4, pp. 714-718.

Okelo et al. "Optimization of extrusion conditions for elimination of mesophilic bacteria during thermal processing of animal feed mash", Animal Feed Science and Technology, 2006, vol. 129, pp. 116-137.

Okelo et al. "Improvements in Reduction of Feed Contamination: An Alternative Monitor of Bacterial Killing During Feed Extrusion", Journal Applied Poultry Research, 2008, vol. 17, pp. 219-228.

Sommers et al. "Inactivation of Listeria Innocua on Frankfurters That Contain Potassium Lactate and Sodium Diacetate by Flash Pasteurization", Journal of Food Science, 2008, vol. 73, No. 2, pp. M72-M74.

Wallace et al. "Thermal Inactivation of Clostridium sporogenes PA 3679 and Bacillus stearothermophilus 1518 in Low-Acid Home-Canned Foods", Journal of Food Science, 1978, vol. 43, No. 6, pp. 1738-1740.

Williams et al. "Lethality of Small-Scale Commercial Dehydrator and Smokehouse/Oven Drying Processes Against *Escherichia coli* O157:H7-, *Salmonella* spp.-, Listeria monocytogenes-, and *Staphylococcus aureus*-inoculated Turkey Jerky and the Ability of a Lactic Acid Bacterium to Serve as a Pathogen Surrogate", Poster presented at the annual meeting of the Institute of Food Technologists, Department of Food Science, The University Wisconsin-Madison, 2,hicago, IL., Jul. 2010.

\* cited by examiner

DECONTAMINATION SURROGATE MICROORGANISMS

CROSS-REFERENCE TO RELATED APPLICATIONS

This Application is a U.S. National Stage Patent Application of International Application No. PCT/EP2017/060186, filed on Apr. 28, 2017 which claims priority from French Patent Application No. 1653914, filed Apr. 29, 2016, the content of both of which is herein incorporated in their entirety by reference.

FIELD OF INVENTION

Strains identified in the claims 4, 5, 9, 10 and 13 have been deposited under the Budapest Treaty on Mar. 2, 2016 at CNCM Collection Nationale de Culture de Microorganismes, Institut Pasteur in Paris (France). Deposit numbers are the following CNCM I-5054, CNCM I-5055, CNCM I-5056, CNCM I-5058, CNCM I-5059, CNCM I-5060, CNCM I-5061, CNCM I-5062 and CNCM I-5063.

The present invention concerns the validation of decontamination processes, and in particular new indicator organisms, as well as mixtures of these microorganisms, used to validate decontamination processes.

STATE OF THE ART

Pasteurization processes are applied in many fields, both for equipment sterilization and for food decontamination, particularly dry food. These processes consist of specific decontamination/sterilization steps or are the concomitant result of a step of a treatment process, such as a step of cooking a food, for example the roasting of products of plant origin.

Products of plant origin, such as almonds and spices, are often contaminated by pathogenic microorganisms present in the environment where they are grown, stored and used and therefore must undergo a decontamination step before use for human consumption. This decontamination is often performed as a temperature treatment of these foods, such as cooking, roasting or drying. However, certain pathogens may be resistant to certain decontamination conditions and it must be confirmed, before the process is implemented, that the decontamination objective will be achieved.

Due to risks of contamination, this validation cannot be done with a pathogenic microorganism. Consequently, use is made of indicator microorganisms, referred to as "surrogates", whose behaviour under the treatment conditions must be similar to that of the pathogenic organism. Preferably, the surrogates will be chosen to be more resistant to the treatment conditions than the pathogens, without behaving too differently from the target pathogens.

These surrogates are generally specific to a particular pathogen in a decontamination process, such as for example *Enterococcus faecium* (ATCC 8459) recommended for the validation of pasteurization processes for almonds potentially contaminated by pathogenic *Salmonella*.

Surrogates are not necessarily microorganisms phylogenetically closer to the target pathogens, such as for example the genus *Citrobacter*, a genus evolutionarily closer to *Salmonella*, which is not described as a surrogate for this pathogen. For example, as a surrogate for *Salmonella*, some have used *Geobacillus stearothermophilus* (ATCC 12980) for the validation of a feed extrusion process (Okelo et al., 2006 and 2008), *Enterococcus faecium* (NRRL B-2354) for the pasteurization of liquids (Annous and Kozempel, 1998) or almonds (ABC, 2007) or for food extrusion (Bianchit, 2014), *Pantoea agglomerans* (SPS 2F-1) for almond roasting (ABC, 2007), *Pantoea dispersa* for the treatment of fresh food by electron beam irradiation (Fudge et al., 2016), *Pediococcus* spp. and *Pediococcus acidilactici* for the preparation of beef jerky (Borowski et al, 2009), the preparation of dried turkey (Williams, 2010) or the extrusion of animal feed (Ceylan and Bautista, 2015), and *Staphylococcus carnosus* (CS-299) for the preparation of ground beef and frankfurter batter (Vasan et al., 2014).

As surrogates for *Clostridium botulinum*, some have used *Clostridium sporogenes* (PA3679, 3676 and 3678) for low-acid foods (Wallace et al. 2006)

As surrogates for *Listeria monocytogenes*, some have used *Listeria innocua* in a pasteurization process for frankfurters (Sommers et al., 2008) or *Escherichia coli* K12 in an irradiation sterilization process for cantaloupes (Rodriguez et al., 2006).

Various non-pathogenic *E. coli* have been described as surrogates for *E. coli* O157:H7 in the treatment of juice (Gurtler, 2010) or beef (Garcia Hernandez et al., 2015).

While the strain *Enterococcus faecium* (NRRL B-2354) has been used for the validation of thermal processes for several low water activity foods, this strain shows much higher heat resistance than a great number of pathogens, including *Salmonella*.

Moreover, save for *Enterococcus faecium*, the strains identified in the prior art are at the level of laboratory tests, often in the form of extemporaneous liquid suspensions, which are not very versatile as for the carriers used and not very suitable for large-scale industrial use which requires the availability of large amounts of viable forms of surrogates ready-to-use on multiple carriers.

There remains a need for surrogates better adapted to decontamination processes and to target pathogens, that can be used alone or in mixtures, that have resistance behaviours closer to the target pathogen(s) and provide more relevant information about the decontamination process in order to validate processes that are more energy efficient and that better protect the structural and/or organoleptic properties of the treated products, and in particular that are suitable for industrial use. The inventors have identified several groups of non-pathogenic microorganisms that meet this need.

DISCLOSURE OF THE INVENTION

The present invention concerns a process for monitoring a decontamination process wherein the decontamination process is implemented in the presence of at least one indicator microorganism, or a mixture of indicator microorganisms, and the behaviour of the indicator microorganism(s) during said decontamination process is observed, characterized in that the indicator microorganism is a non-pathogenic microorganism selected from non-pathogenic Enterobacteriaceae of the genus *Enterobacter*, the genus *Erwinia* or the genus *Pantoea*.

The present invention also concerns indicator microorganisms useful as surrogates in a process for monitoring a decontamination process, selected from *Enterobacter hormaechei* CNCM I-5058, *Pantoea agglomerans* CNCM I-5059, *Enterobacter mori* CNCM I-5060, *Pantoea calida* CNCM I-5061, *Erwinia persicina* CNCM I-5062, *Erwinia persicina* CNCM I-5063, *Pantoea agglomerans* CNCM I-5054, *Pantoea agglomerans* CNCM I-5055, *Pantoea calida* CNCM I-5056.

It also concerns a kit for monitoring a decontamination process, comprising at least one indicator microorganism according to the invention and a suitable carrier for use in the decontamination process.

DETAILED DESCRIPTION OF THE INVENTION

The present invention concerns a process for monitoring a decontamination process wherein the decontamination process is implemented in the presence of at least one indicator microorganism, or a mixture of indicator microorganisms, and the behaviour of said indicator microorganism(s) is observed during said decontamination process, characterized in that the indicator microorganism is a non-pathogenic microorganism selected from non-pathogenic Enterobacteriaceae of the genus *Enterobacter*, the genus *Erwinia* or the genus *Pantoea*.

"Microorganism" means a group of several individual microorganisms of the same species. Preferably, the microorganisms are suitable for industrial use, i.e. they can be produced in large quantities by fermentation, up to at least $10^{10}$ CFU/g, more preferably up to at least $10^{11}$ CFU/g.

Particular examples include bacteria selected from the species *Enterobacter hormaechei, Enterobacter mori, Erwinia persicina, Pantoea agglomerans, Pantoea calida,* and *Pantoea gaviniae*, which are non-pathogenic, preferably industrially producible, more particularly selected from the following species deposited at the CNCM under the Budapest Treaty: *Enterobacter hormaechei* CNCM I-5058, *Pantoea agglomerans* CNCM I-5059, *Enterobacter mori* CNCM I-5060, *Pantoea calida* CNCM I-5061, *Erwinia persicina* CNCM I-5062, *Erwinia persicina* CNCM I-5063, *Pantoea agglomerans* CNCM I-5054, *Pantoea agglomerans* CNCM I-5055, *Pantoea calida* CNCM I-5056.

According to a first embodiment of the invention, at least one indicator microorganism is selected from non-pathogenic Enterobacteriaceae of the genus *Pantoea*, the genus *Enterobacter* or the genus *Erwinia* and mixtures thereof.

Advantageously, a mixture of at least 2 indicator microorganisms is used (multiplex validation), in particular at least 2 indicator microorganisms selected from non-pathogenic Enterobacteriaceae of the genus *Pantoea*, the genus *Enterobacter* or the genus *Erwinia* and mixtures thereof. According to a more specific embodiment of the invention, the mixture comprises at least one indicator microorganism selected from non-pathogenic Enterobacteriaceae of the genus *Pantoea* and at least one indicator microorganism selected from non-pathogenic Enterobacteriaceae of the genus *Enterobacter* or the genus *Erwinia* as defined above.

The advantage of these non-pathogenic indicator microorganisms is that they are more resistant to the conditions of different decontamination processes than at least one target pathogenic organism. These target pathogenic organisms are microorganisms responsible for contamination, in particular pathogenic bacteria of the genera *Salmonella, Escherichia, Bacillus, Listeria, Campylobacter, Cronobacter*, etc. The decontamination process to which the monitoring process is directed is aimed at removing all these pathogens if present in the treated product.

Advantageously, the indicator microorganisms have a thermal resistance superior to *Salmonella* under low aw conditions and are packaged on an inert matrix.

"Low aw" preferably means water activity below 0.85 (CAC/RCP 75-2015, Codex *Alimentarius*).

"Inert matrix" preferably means a suitable carrier for the preservation and use of indicator microorganisms, in particular in dry form. The carrier is inert, i.e. does not interact with the metabolism of bacteria in dry form allowing optimal preservation over time.

In the decontamination process, the indicator microorganism will be used in an appropriate form, corresponding to the form of the target pathogen likely to be present in the product to be decontaminated, in particular in vegetative and/or dry vegetative form.

"Dry form" or "dry vegetative form" means vegetative bacteria which have undergone a drying process enabling them to be preserved for a specified period without altering their resistance characteristics.

The indicator microorganisms produced by fermentation are then dried for preservation using techniques known to the skilled person, such as lyophilization, atomization or drying.

Decontamination processes generally include one or more steps of pasteurization, drying, extrusion, roasting, cooking, sterilization, autoclaving and steam treatments.

These processes are well known to the skilled person, notably pasteurization, drying, extrusion, roasting, cooking, sterilization, autoclaving, steam treatments, pulsed light, high-pressure treatments, or irradiation, gas sterilization (EtO, ppo, ozone) and disinfectants (bleach, peracetic acid, etc.), in particular for the treatment of natural or manufactured products, such as nuts, aromatic herbs, seeds, spices, food powders, pet and livestock feed, cereals, etc.

The surrogates and mixtures of surrogates according to the invention can be used, depending on the foods and processes selected, to validate decontamination of pathogens such as *Salmonella, Escherichia coli, Bacillus, Listeria, Campylobacter, Cronobacter sakazakii*, etc.

To that end, the indicator microorganism will be used with a suitable carrier, well known to the skilled person, which is preferably inert, for example with cryoprotectants such as maltodextrin and/or milk powder and solid carriers such as talc, silica and/or activated carbon. The carrier may also include a marker which makes it easy to find contaminated products (for example a visible or UV/IR-fluorescent dye), in particular any marker making it possible to distinguish contaminated areas from others (magnetic, isotopic, chemical marking, etc.).

The use of an appropriate carrier allows standardization in the use of the microorganisms on different matrices by providing better stability of the microorganisms and avoiding the need to validate the stability of each indicator microorganism on each carrier after inoculation. It facilitates the implementation of the process according to the invention.

The invention also concerns a dry composition comprising an indicator microorganism and a suitable carrier, as defined above and below.

The composition advantageously comprises an indicator microorganism content of at least $10^{10}$ CFU/g dry composition.

The dry composition is advantageously a powder with a water activity of 0.3 or below.

These compositions are prepared according to methods known to the skilled person by mixing the indicator microorganisms in dry form with the carrier, in the desired proportions, using conventional techniques. According to another embodiment, the indicator microorganisms are mixed with the appropriate carrier and the mixture is then dried for preservation.

In general, the indicator microorganisms with their carrier are added to the products to be decontaminated in appropriate amounts to allow verification of the efficacy of the decontamination process.

The microorganisms and their carrier may, if need be, undergo a treatment prior to the decontamination, similar to that undergone by the product to be decontaminated, i.e. which will mimic the known product contamination processes. For example, natural products that are ground (spices in particular) can be ground after adding the indicator microorganisms on their carrier to produce powders while recreating the classic natural product contamination conditions.

The monitoring process according to the invention can be implemented before any decontamination process is implemented on the product to be decontaminated, in order to validate the efficacy of the decontamination process (validation process). It can also be used during decontamination operations on the product to be decontaminated, as an indicator of decontamination or as an indicator of conformity of implementation of the decontamination process (monitoring process).

The process according to the invention, whether a validation or monitoring process, can be implemented under the responsibility of the person carrying out the decontamination or under that of an inspection or accreditation body.

The surrogate microorganisms will be advantageously supplied in kit form, with their carrier for use and, if need be, a set of instructions.

Observation of the behaviour of the indicator microorganism generally consists in monitoring the presence of viable individuals during and/or after the decontamination process. The methods used are known to the skilled person: counting colonies on agar and/or molecular methods such as PCR and/or qRT-PCR, or microorganism detection tests such as immunological tests, for example tests using SPR technologies, such as those developed by the company PRESTODIAG, or phage-based detection tests.

The present invention also concerns an indicator microorganism useful as a surrogate in a process for monitoring a decontamination process, selected from *Enterobacter hormaechei* CNCM I-5058, *Pantoea agglomerans* CNCM I-5059, *Enterobacter mori* CNCM I-5060, *Pantoea calida* CNCM I-5061, *Erwinia persicina* CNCM I-5062, *Erwinia persicina* CNCM I-5063, *Pantoea agglomerans* CNCM I-5054, *Pantoea agglomerans* CNCM I-5055, *Pantoea calida* CNCM I-5056. It concerns more particularly these isolated microorganisms, or in vegetative form and/or dry vegetative form. The invention also concerns a mixture of microorganisms comprising at least 2 of the species of microorganisms above, in all their 2-by-2 combinations, up to a mixture comprising the 10 species of microorganisms above. The invention also concerns a composition comprising a microorganism above or a mixture of said microorganisms and a suitable carrier, in particular an inert carrier as defined above.

According to a preferred embodiment of the invention, the surrogate is selected from *Pantoea agglomerans* CNCM I-5054, *Pantoea agglomerans* CNCM I-5055, *Pantoea calida* CNCM I-5056 or a mixture of surrogates comprising at least one surrogate selected from *Pantoea agglomerans* CNCM I-5054, *Pantoea agglomerans* CNCM I-5055, *Pantoea calida* CNCM I-5056.

The invention also concerns a kit for monitoring a decontamination process, characterized in that it comprises at least one microorganism above and a suitable carrier as defined above for use in the decontamination process and, if need be, a set of instructions.

The invention also concerns the use of at least one microorganism selected from non-pathogenic Enterobacteriaceae of the genus *Enterobacter*, the genus *Erwinia* or the genus *Pantoea* as defined above, or a kit according to the invention, for monitoring a decontamination process, notably for validation prior to the process or for monitoring during the process.

EXAMPLES

Figure 1:
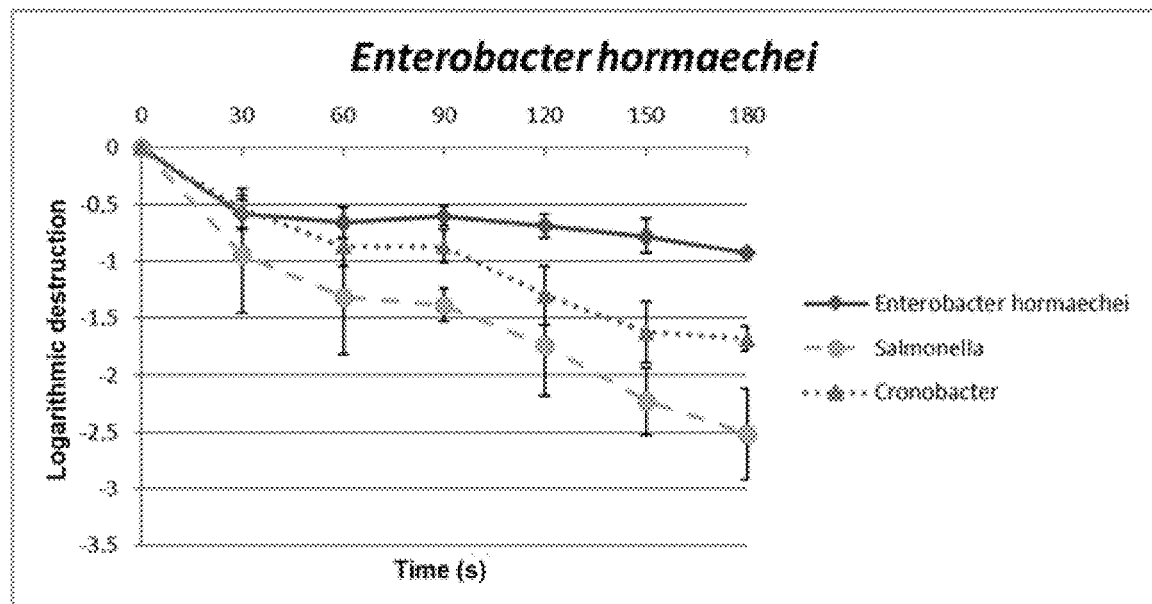
FIGS. 1 to 4 show the resistance curves of different surrogate microorganisms in comparison with the pathogens *Salmonella* and *Cronobacter sakazakii*.
Figure 2:
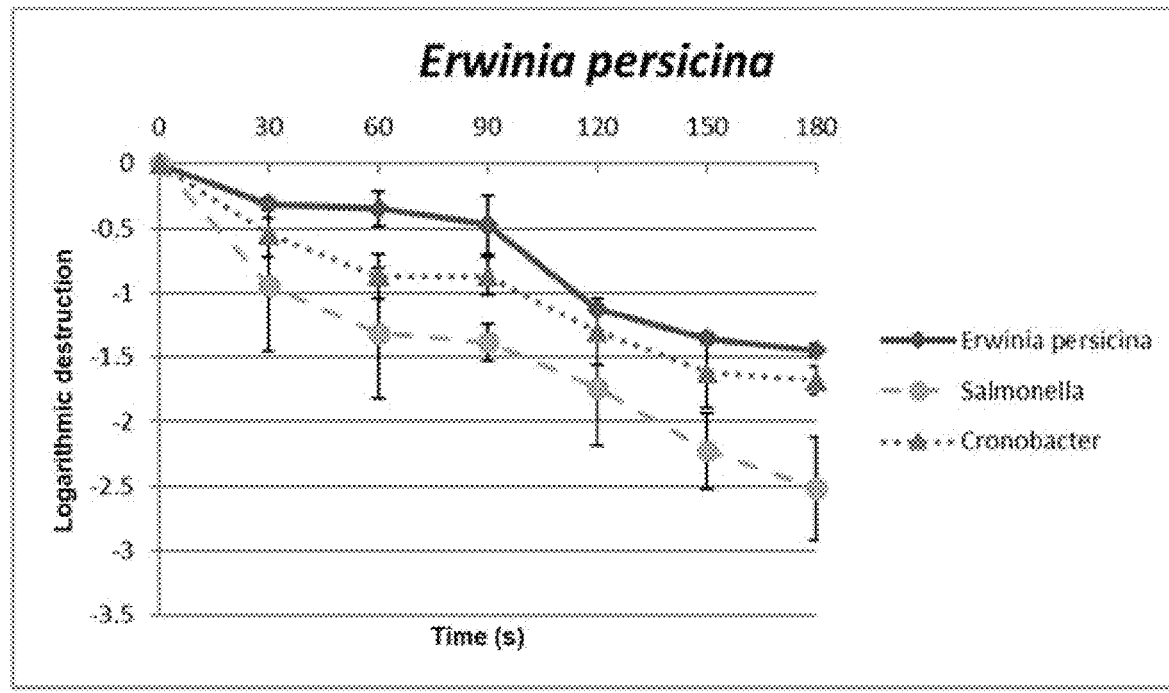
Figure 3:
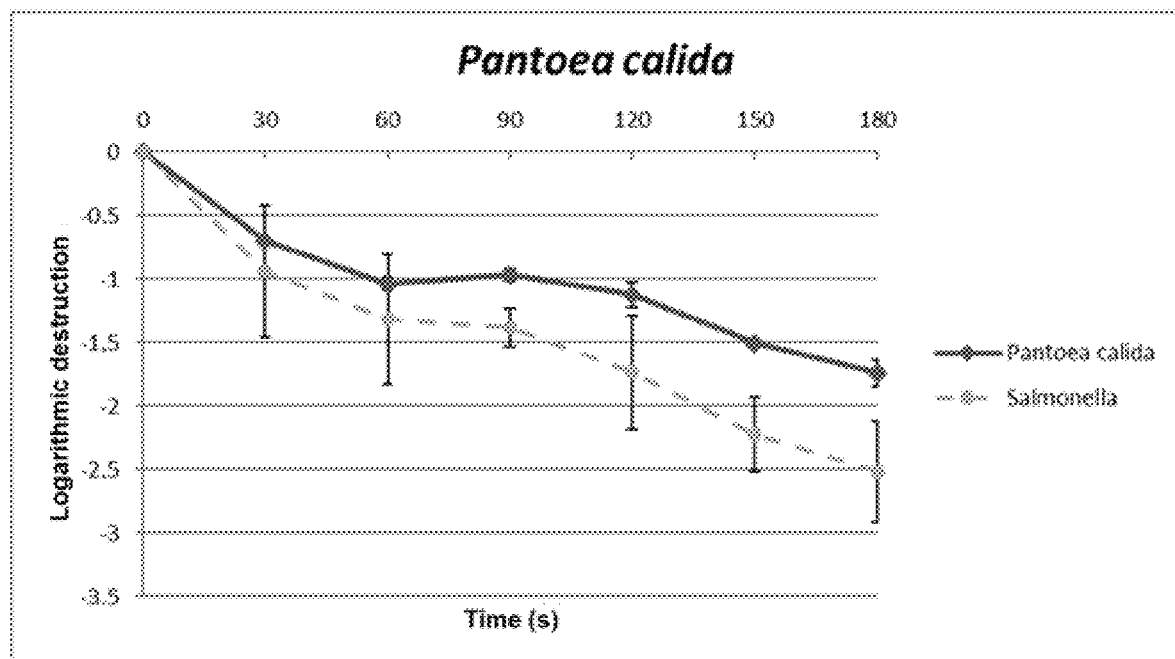
Figure 4:
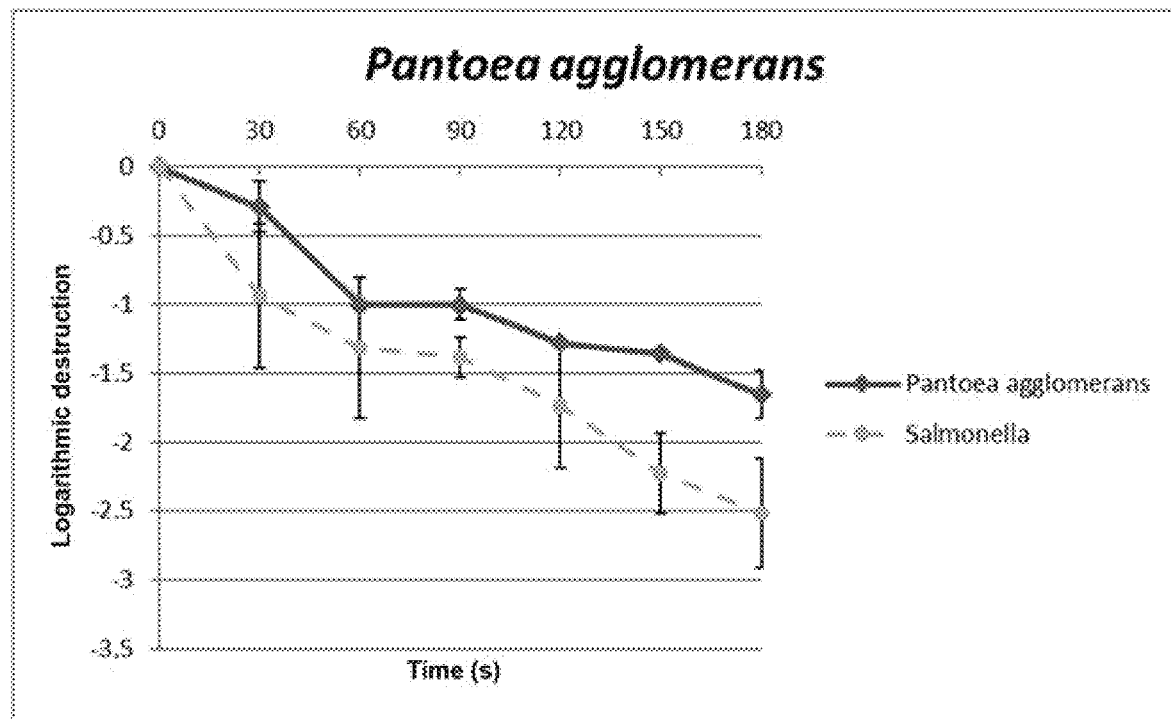

Example I. Isolation and Selection of Microorganisms

1. Isolation of Environmental Enterobacteriaceae

A 0.5 g sample of dry products was placed in a 1.5 mL Eppendorf tube and heat treated in a dry bath for 15 min at 95° C. After cooling to room temperature, 1 mL of concentrated PBS (aw=0.950) was added before vortexing for 30 s. Successive 1/10 dilutions were prepared in PBS (aw=0.995) before spreading on Violet Red Bile Glucose Agar (VRBG) in an amount of 100 µL per plate. After incubation at 37° C. for 24-48 h, colonies were isolated on Tryptic Soya Agar (TSA) and incubated again at 37° C. for 24 h.

2. Identification of Environmental Enterobacteriaceae

Amplifications of 16S rDNA of each isolate were performed directly by sub-culturing the colonies in the PCR mix. The primers used were: 27F (5'-AGA GTT TGA TCM TGG CTC AG-3') and 1492R (5'-TAC GGH TAC CTT GTT ACG ACT T-3'). To perform the PCR, the "Taq Core Kit" (Quiagen, France) was used. Briefly, the PCR mix (50 µL per reaction) for a colony is composed of 0.5 µM of each primer, 0.2 mM dNTP mix, 0.75 U Taq polymerase and 1× buffer containing $MgCl_2$. The amplification was verified by 1% agarose gel electrophoresis before sequencing the PCR products by the Sanger method. The sequences obtained were used to search the NCBI database (BLASTn) and in this way the isolates were identified. Twelve isolates were then selected.

3. Thermal Challenge a. Strain Culture Conditions

All cultures were stored in Tryptic Soy Broth (TSB, Sigma-Aldrich) with 20% glycerol (Sigma-Aldrich) at −80° C. To restart the cultures, the bacteria were inoculated on TSA for 24 h at 37° C. and then five colonies of each bacterium were sub-cultured in 50 mL of TSB before being incubated at 37° C. for 8 h. These bacterial suspensions are then diluted in 50 mL of fresh TSB to achieve an optical density (OD) of 0.01 at 600 nm. Cultures in the stationary growth phase are thus obtained after 20 h at 37° C.

b. Inoculation of Milk Powder

For each bacterium, the 50 mL cultures are centrifuged (3400 g, 10 min at 25° C.) then washed twice in 25 mL of PBS. Finally, a final centrifugation is performed, the supernatant is removed, and the pellets are weighed. Milk powder (26% fat) is added to each pellet with a ratio of 1:20 ($m_{pellet}$:$m_{powder}$) and the whole is homogenized using a mortar. Inoculated milk powder is thus obtained.

c. Drying Process

For the inoculated milk powder, airtight containers, containing saturated salt solutions for controlling water activity and thus the relative humidity of the atmosphere, are used. Lithium chloride, potassium acetate, potassium carbonate and sodium bromide were used to obtain water activity of 0.11, 0.25, 0.44 and 0.58. The atmospheres thus obtained are maintained under convection using a fan. For each strain, the inoculated powder is spread on Petri dishes (about 5 g per dish). These dishes, without lids, are then placed in the airtight containers for 16 h to reach equilibrium water activity. All drying was carried out at room temperature.

d. Heat Treatment 0.1 g of dried inoculated milk powder is placed in a 0.2 mL tube and treated at different temperatures (85° C., 90° C., 95° C. and 100° C.) for a given time (0 s, 30 s, 60 s, 90 s, 120 s, 150 s and 180 s) using a thermocycler before being cooled to 4° C. The samples are rehydrated by adding 1 mL of PBS before vortexing for 30 s. A CFU count was performed after incubation on TSA for 24 h at 37° C. The results are expressed as $\log_{10}(N/N_0)$, where N is the CFU count after treatment and $N_0$ is the initial CFU count of the milk powder before treatment (t=0 s).

| Species | Deposit No. | D-value |
|---|---|---|
| Enterococcus faecium | ATCC 8459 | 23.69 |
| Enterobacter hormaechei | CNCM I-5058 | 4.36 |
| Pantoea agglomerans | CNCM I-5059 | 1.81 |
| Enterobacter mori | CNCM I-5060 | 3.95 |
| Pantoea calida | CNCM I-5061 | 2.03 |
| Erwinia persicina | CNCM I-5062 | 1.74 |
| Erwinia persicina | CNCM I-5063 | 1.96 |
| Pantoea agglomerans | CNCM I-5054 | 1.27 |
| Pantoea agglomerans | CNCM I-5055 | 1.33 |
| Pantoea calida | CNCM I-5056 | 1.14 |
| Salmonella Typhimurium | DSM 10506 | 1.21 |
| Cronobacter sakazakii | PAC 103183T | 1.13 |

Example II. Validation of a Decontamination Process

The technology most commonly used in the decontamination sector, in both food-processing and pharmaceutical industries, remains autoclaves. It is thus possible to heat the product in a chamber, while either static or in motion, simply by condensation of steam on said product. The product can then be dried by a combination of heating and vacuum treatment. There are hundreds of autoclave manufacturers worldwide, a certain number of which work on pasteurization of dry food products.

The classic pasteurization cycle for these devices consists of the following steps:
Phase 1: Air removal. Several cycles are performed to remove as much air as possible. This step is necessary to allow steam to penetrate through the product.
Phase 2: Heating. Steam is injected in order to heat the product. The chamber enclosure is also heated by electrical resistance to prevent condensation.
Phase 3: Pasteurization. Once the product has reached a target temperature, there is a holding time at that temperature. The treatment time-temperature pair is defined upstream of the validation work. The time-temperature pair is crucial for the efficacy of the treatment.
Phase 4: Drying. The steam is removed by vacuum drying.
Phase 5: Aeration. The chamber is ventilated by a stream of filtered air at atmospheric pressure The product is then discharged from the chamber in the direction of production in order to prevent contact with untreated material. Depending on the chosen cycle, its temperature at the end of the process varies from 30 to 50° C. The product is not packaged until it has returned to room temperature because bagging when too hot could cause germs to develop.

In situ validation of a decontamination process generally comprises three main steps:
Preparatory phase: process evaluation, risk assessment, model germ qualification, development of the in situ validation protocol
Execution phase: inoculation of the product to be tested, execution of validation "batches", sample recovery
Synthesis phase: counting of the model germs, writing of the analysis report and/or validation report During the development of the validation protocol, the following are defined, among other things:
Whether or not it is necessary to pre-treat the product to be tested (for example: irradiation)
The number of validation batches and the duration of each validation batch to be prepared
The amount of product to be inoculated (from 25 g to >10 t depending on the decontamination processes and the validation method selected)
The desired level of inoculation and the amount of model germ to be used
The method for inoculating the product with the model germ (there are various possibilities, including inoculation in the laboratory, directly in the factory, at a service provider, etc.)
The sampling method at the end of the production line (including, among other things, sample number and size)
The method for counting the model germ (among other things: selective or non-selective medium)

The answers to these various questions depend essentially on three parameters: type of process to be validated, target pathogen, product to be inoculated.

Thus, the validation "kit" provided may vary in particular in:
Mixing level of the model germ with the product to be tested (the model germ may be supplied in concentrated form to be inoculated or in pre-mixed form with the product)
Concentration level of model germ
Amount supplied (from several kgs/tens of kgs for the concentrated form to several tons for the pre-mixed version)

Example III. Production of Indicator Microorganisms by Fermentation

Pre-Culture

Pre-culture of the surrogate microorganism should be started between 16 h and 24 h before fermentation. The Erlenmeyer flask containing the culture medium is inoculated with surrogate microorganism at a ratio of 1:5. The pre-culture is incubated at 37° C. with shaking at 150 rpm.

Fermentation Process

Culture begins when the entire pre-culture has been inoculated in the fermenter. The shaking, aeration and substrate addition conditions are as follows:

pH maintained by a base throughout the culture

Temperature maintained at 37° C. by the heating double-walled enclosure and/or jacket, and throughout the culture Oxygen saturation of the initial medium before inoculation (pO2>90%)

Shaking (rpm): 200-500.

Aeration (L/min): 1-3.

At the end of the culture, the fermenter culture medium is transferred to sterile bottles in order to recover all biomass.

Biomass Recovery and Preparation in Dry Form

Biomass is recovered by centrifugation or by another technique such as ultrafiltration that allows the cells to be separated from the culture medium.

Cryoprotectant, once sterilized, is added at a volume ratio of 1:1 to the biomass and the whole is frozen at −80° C. for at least 24 h with a view to potential lyophilization.

Example IV. Use of Indicator Microorganisms on Different Dry Products

The objective of these examples is to show the thermal destruction kinetics of different indicator microorganisms and to compare them to that of *Salmonella* in different products with low water activity.

Microorganisms Tested

Four different *Salmonella* serotypes (*Senftenberg, Enteridis, Typhimurium* and *Mbandaka*), inoculated individually or in cocktail form, are used as control strains for comparison with the model microorganisms tested.

The thermal resistance of two different indicator microorganisms is tested:

*Enterobacter hormaechei* CNCM I-5058, dry preparation.

*Pantoea agglomerans* CNCM I-5055, dry preparation.

The strain *Enterococcus faecium* (ATCC® 8459™) was used as reference strain because it is widely used as a biological tracer in validation of dry food treatment processes.

Inoculation Protocols

Two different methods are used to inoculate the different products:

Liquid inoculation of the pathogens: broth cultures of the four *Salmonella* serotypes prepared the day before are used independently to inoculate the products produced (paprika powder, milk powder and macadamia nuts). After inoculation the product is placed under a type II biological safety cabinet in order to equilibrate its water activity.

Dry inoculation of the indicator microorganisms: the different products (paprika powder, milk powder and macadamia nuts) were inoculated independently with the surrogate microorganisms in dry form following production by fermentation and stabilization by lyophilization. No resting time is required after inoculation with the model microorganisms in dry form, which results in very little modification of the product's properties (aw, moisture percentage, etc.) and allows faster use of the inoculated matrices.

Results

Figure 5A:
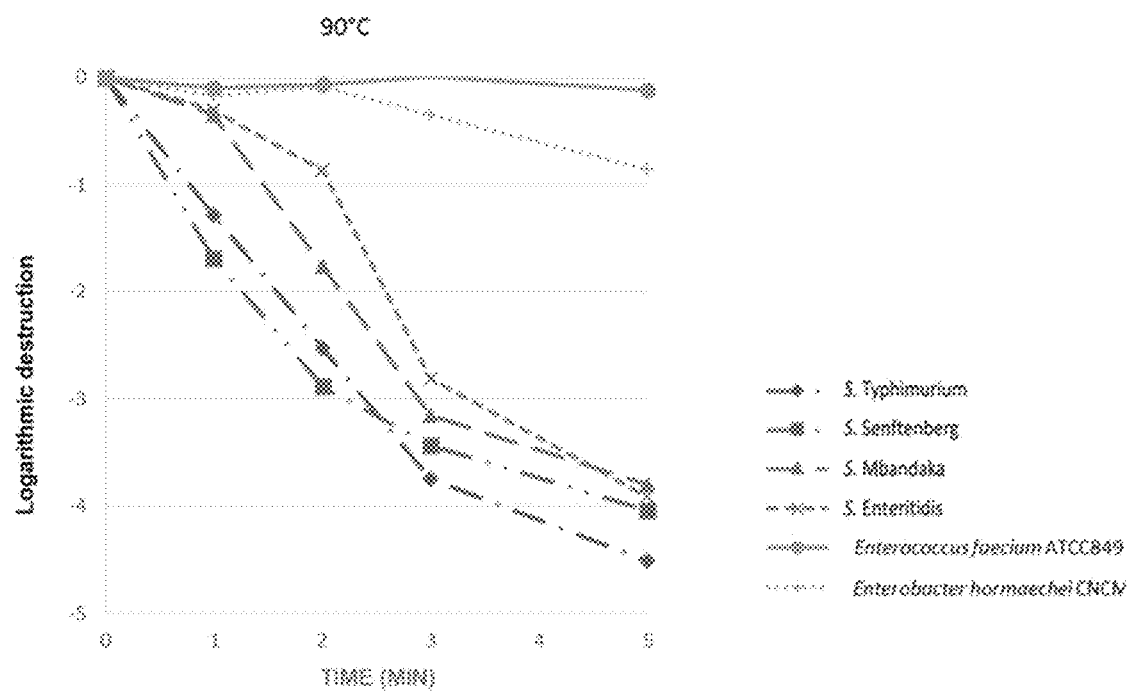
FIGS. 5 to 7 show the cell destruction dynamics of indicator microorganisms according to the invention, of the reference strain *E. faecium* ATCC 8459 and of four *Salmonella* serotypes on different products.
Figure 5B:
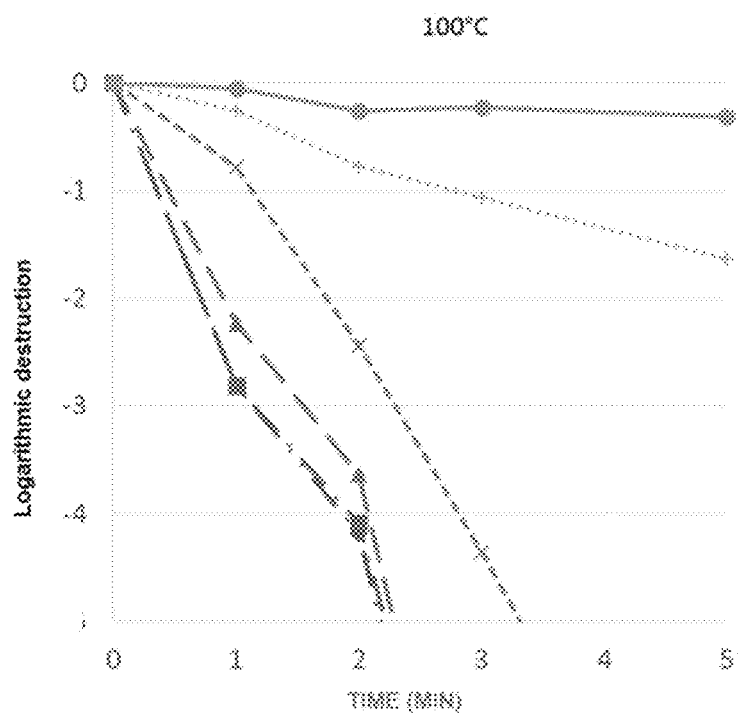

The cell destruction dynamics at 90° C. and 100° C. of strain *E. hormaechei* CNCM I-5058, reference strain *E. faecium* ATCC 8459 and the 4 *Salmonella* serotypes on paprika powder are shown in FIGS. 5A (treatment at 90° C.) and 5B (treatment at 100° C.). The results show in all cases that the behaviour of the model microorganism *E. hormaechei* CNCM I-5058 is always closer to all *Salmonella* serotypes, thereby confirming its nature as a surrogate germ well suited to the target pathogen on the product in question.

Figure 6A:
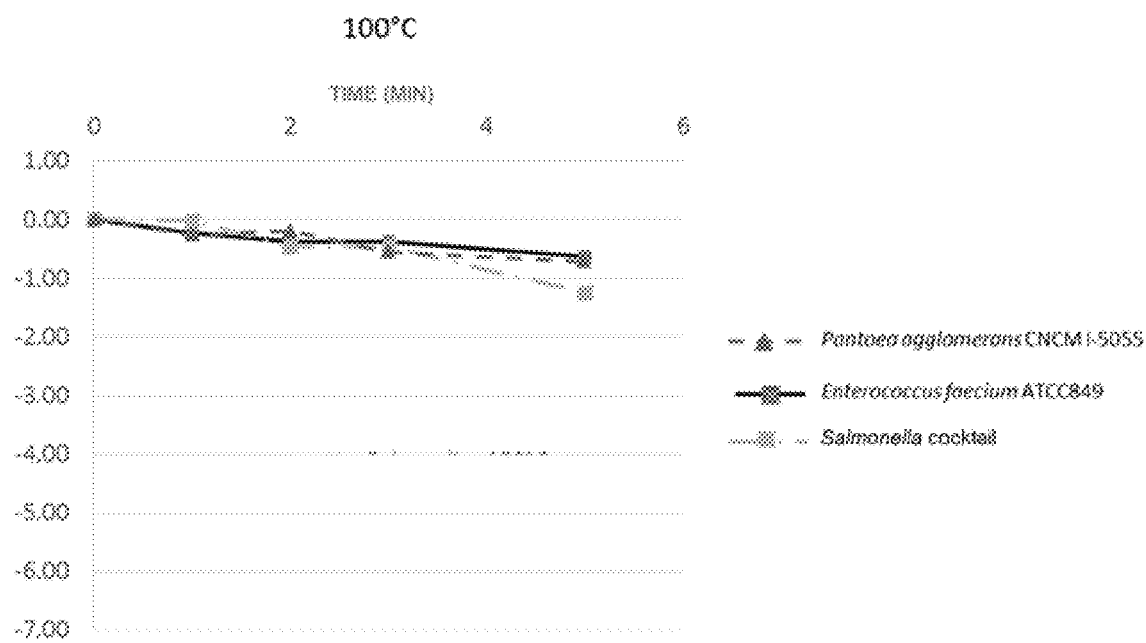
Figure 6B:
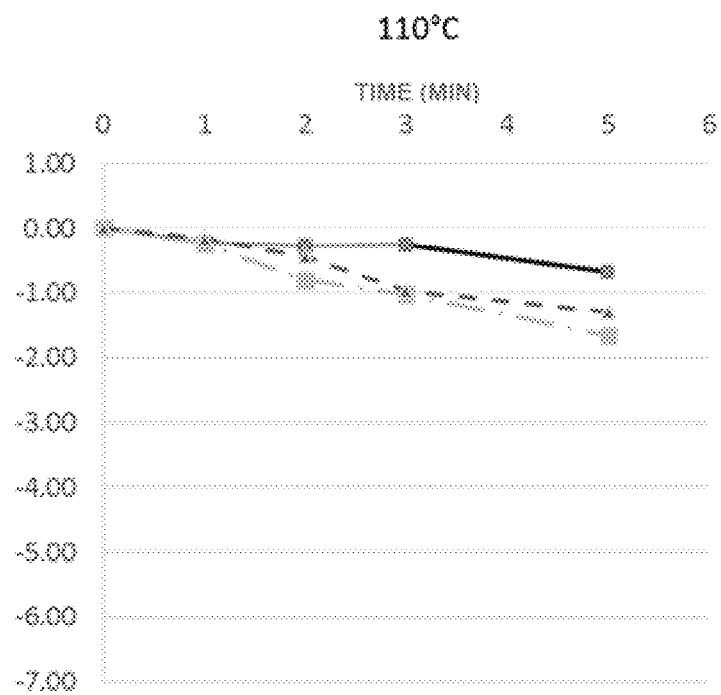

The cell destruction dynamics at 100° C. and 110° C. of strain *P. agglomerans* CNCM I-5055, reference strain *E. faecium* ATCC 8459 and the 4 *Salmonella* serotypes in cocktail form on macadamia nuts are shown in FIGS. 6A (treatment at 100° C.) and 6B (treatment at 110° C.). The results show that the behaviour of the model microorganism *P. agglomerans* CNCM I-5055 is closer to all *Salmonella* serotypes, thereby confirming its nature as a surrogate germ well suited to the target pathogen on the product in question.

Figure 7A:
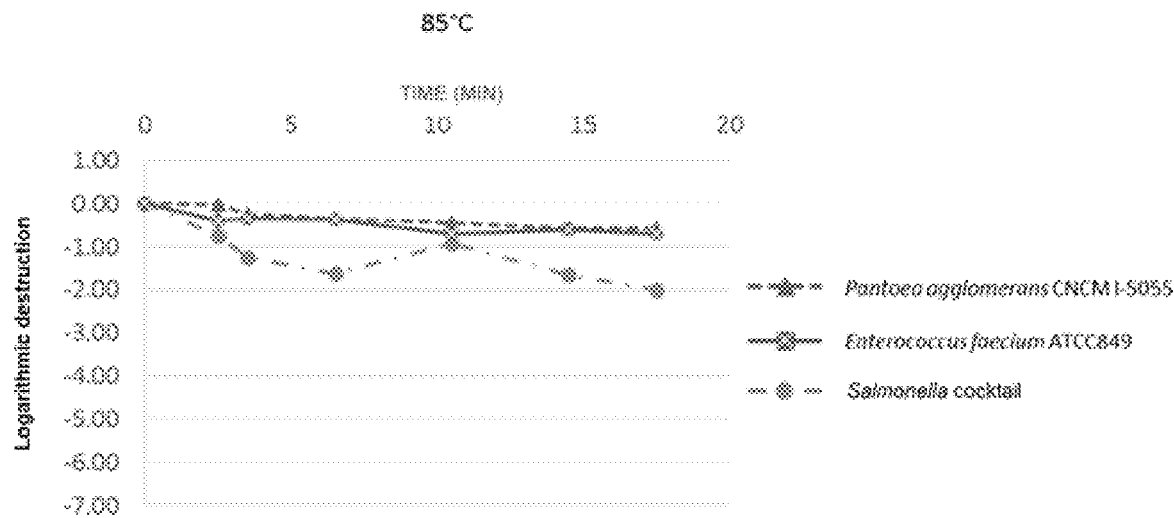
Figure 7B:
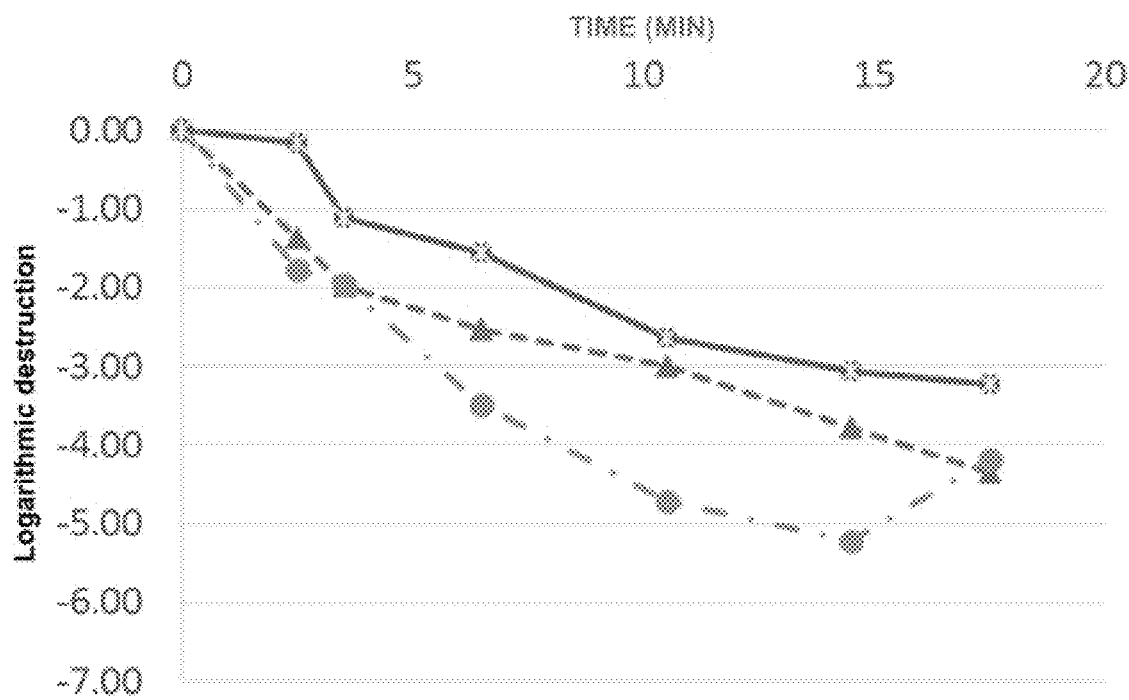

The cell destruction dynamics at 85° C. and 100° C. of strain *P. agglomerans* CNCM I-5055, reference strain *E. faecium* ATCC 8459 and the 4 *Salmonella* serotypes in cocktail form on skim milk powder are shown in FIGS. 7A (treatment at 85° C.) and 7B (treatment at 100° C.). The results show that the behaviour of the model microorganism *P. agglomerans* CNCM I-5055 is closer to all *Salmonella* serotypes, thereby confirming its nature as a surrogate germ well suited to the target pathogen on the product in question.

REFERENCES

Annous, 1998 Annous B A, Kozempel M F. 1998. Influence of growth medium on thermal resistance of *Pediococcus* sp. NRRL B-2354 (formerly *Micrococcus freudenreichii*) in liquid foods. J Food Prot. 61(5):578-81.

Bianchini & al., Use of *Enterococcus faecium* as a Surrogate for *Salmonella enterica* during Extrusion of a Balanced Carbohydrate-Protein Meal. J. Food Prot., Vol. 77, No. 1

Borowski, A. G., S. C. Ingham, and B. H. Ingham, 2009. Validation of ground- and formed beef jerky processes using commercial lactic acid bacteria starter cultures as pathogen surrogates. Journal of Food Protection 72: 1234-1247

Enache & al., Development of a Dry Inoculation Method for Thermal Challenge Studies in Low-Moisture Foods by Using Talc as a Carrier for *Salmonella* and a Surrogate (*Enterococcus faecium*). Journal of Food Protection, 2015. 78: 1106-1112

Erdogan & al., Evaluating *Pediococcus acidilactici* and *Enterococcus faecium* NRRL B-2354 as Thermal Surrogate Microorganisms for *Salmonella* for In-Plant Validation Studies of Low-Moisture Pet Food Products. Journal of Food Protection, Vol. 78, No. 5, 2015, Pages 934-939.

Fudge & al., The Isolation and Identification of *Pantoea dispersa* strain JFS as a Non-Pathogenic Surrogate for *Salmonella Typhimurium* Phage Type 42 in Flour, International Journal of Food Microbiology 219 (2016) 1-6

Garcia Hernandez & al., 2015 Garcia-Hernandez R, McMullen L, Ganzle M G. 2015. Development and validation of a surrogate strain cocktail to evaluate bactericidal effects of pressure on verotoxigenic *Escherichia coli*. Int J Food Microbiol. 205:16-22.

Guidelines for Using *Enterococcus faecium* NRRL B-2354 as a Surrogate Microorganism in Almond Process Validation. Almond Board of California Guideline, October 2007 (ABC, 2007).

Gurtler & al., Selection of surrogate bacteria in place of *E. coli* O157:H7 and *Salmonella Typhimurium* for pulsed electric field treatment of orange juice. International Journal of Food Microbiology 139 (2010) 1-8

Kopit. B. Kim, R. J. Siezen, L. J. Harris, and M. Marco. & al., Safety of the Surrogate Microorganism *Enterococcus faecium* NRRL B-2354 for Use in Thermal Process Validation, Appl. Environ. Microbiol. 2014, 80(6):1899. DOI: 10.1128/AEM.03859-13.

Niebuhr & al., Evaluation of non-pathogenic surrogate bacteria as process validation indicators for *Salmonella* enteric for selected antimicrobial treatments, cold storage and fermentation in meat, J Food Prot. 2008 April; 71(4):714-8.

Okelo, P. O., D. D. Wagner, L. E. Carr, F. W. Wheaton, L. W. Douglass, S. W. Joseph. 2006. Optimization of extrusion conditions for elimination of mesophilic bacteria during thermal processing of animal feed mash. Animal Feed Science and Technology 129:116-137.

Okelo, P. O., S. W. Joseph, D. D. Wagner, F. W. Wheaton, L. W. Douglass, and L. E. Carr, 2008. Improvements in Reduction of Feed Contamination: An Alternative Monitor of Bacterial Killing During Feed Extrusion. Journal Applied Poultry Research 17: 219-228.

Rodriguez et al., Surrogates for validation of electron beam irradiation of foods, International Journal of Food Microbiology, 110 (2006) 117-122

Sommers C H, Geveke D J and, Fan X. Inactivation of *Listeria Innocua* on Frankfurters That Contain Potassium Lactate and Sodium Diacetate by Flash Pasteurization. 2008. J Food Sci 73 (2), M72-M74. 3 2008

Vasan et al., 2014 Vasan, A., R. Geier, S. C. Ingham, and B. H. Ingham. 2014. Thermal tolerance of O157 and non-O157 Shiga toxigenic strains of *Escherichia coli, Salmonella*, and potential pathogen surrogates, in frankfurter batter and ground beef of varying fat levels. Journal of Food Protection. 77:1501-11.

Larson and Johnson. 2003 Wallace M, Larson K, Wolf I, Thompson D and Zottola E. Thermal inactivation of *Clostridium sporogenes* PA 3679 and *Bacillus stearothermophilus* 1518 in low-acid home-canned foods. 2006 Journal of Food Science 43(6):1738-1740.

Williams, 2010 Williams, P., W. M. Leong, B. H. Ingham, S. C. Ingham, 2010. Lethality of Small-Scale Commercial Dehydrator and Smokehouse/Oven Drying Processes Against *Escherichia coli* O157:H7-, *Salmonella* spp.-, *Listeria monocytogenes*-, and *Staphylococcus aureus*-inoculated Turkey Jerky and the Ability of a Lactic Acid Bacterium to Serve as a Pathogen Surrogate. Poster presented at the annual meeting of the Institute of Food Technologists. Chicago, Ill. July 2010.

The invention claimed is:

1. A process for controlling contamination of a medium the process comprising:

a) adding at least one indicator microorganism to the medium;

b) performing a decontamination process to the medium of step a); and c) determining the presence of the indicator microorganism at the end of the decontamination process;

wherein the absence of the indicator microorganism at the end of the decontamination process confirms that contamination is controlled;

wherein the at least one indicator microorganism is selected from *Enterobacter hormaechei* CNCM I-5058, *Enterobacter mori* CNCM I-5060, *Pantoea calida* CNCM I-5061, *Envinia persicina* CNCM I-5062, *Envinia persicina CNCM* I-5063, *Pantoea calida* CNCM I-5056, and mixtures thereof .

2. The process according to claim 1, wherein the indicator microorganisms are used in dry vegetative form.

3. The process according to claim 1, wherein the indicator microorganisms are used dry on an inert carrier.

4. The process according to claim 1, wherein the at least one indicator microorganism is *Pantoea calida* CNCM I-5056.

5. The process according to claim 1, wherein a mixture of at least 2 indicator microorganisms is used.

6. The process according to claim 1, wherein the decontamination process comprises one or more steps of pasteurization, drying, extrusion, roasting, cooking, sterilization, autoclaving and steam treatments.

7. The process according to claim 1, wherein the decontamination process is aimed at removing one or more target pathogenic microorganisms selected from *Salmonella, Escherichia coli, Bacillus, Listeria, Campylobacter, Cronobacter sakazakii.*

8. The process according to claim 1, wherein the indicator microorganism is *Enterobacter hormaechei* CNCM I-5058.

9. The process according to claim 1, wherein the indicator microorganism is *Enterobacter mori* CNCM I-5060.

10. The process according to claim 1, wherein the indicator microorganism is *Pantoea calida* CNCM I-5061.

11. The process according to claim 1, wherein the indicator microorganism is *Erwinia persicina* CNCM I-5062.

12. The process according to claim 1, wherein the indicator microorganism useful as surrogate is *Erwinia persicina* CNCM I-5063.

13. The process according to claim 1, wherein the indicator microorganism is *Pantoea calida* CNCM I-5056.

14. The process according to claim 1, wherein the indicator microorganism content is of at least $10^{10}$ CFU/g dry composition.

* * * * *